US00PP10911P

United States Patent [19]

Lim

[11] Patent Number: Plant 10,911

[45] Date of Patent: May 25, 1999

[54] PEACH TREE NAMED 'BAEKYAKDO'

[76] Inventor: Jung-Kyoung Lim, 637-1 Woulhari, Seomyun, Yunkikun, Chungnam, Rep. of Korea

[21] Appl. No.: 08/862,645

[22] Filed: May 23, 1997

[51] Int. Cl.[6] ..... A01H 5/00

[52] U.S. Cl. ..... Plt./195

[58] Field of Search ..... Plt./42.1, 40.1

[56] References Cited

FOREIGN PATENT DOCUMENTS 052872 2/1992 Rep. of Korea .

OTHER PUBLICATIONS

Kim, et al., (1966) "The New Peach Cultivar "Yumyeong"", (Report of the) Horticultural Experiment Station, Suweon, Korea.

*Primary Examiner*—Howard J. Locker

*Attorney, Agent, or Firm*—Pepper Hamilton LLP

[57] ABSTRACT

A new and distinct variety of peach tree (*Prunus persica*) with the following combination of unique and desirable characteristics:

1. Heavy and regular production of fruit;
2. Production of very firm, white flesh fruit with good handling and shipping quality;
3. Fruit that will stay firm on the 10 to 17 days after maturity (shipping ripe);
4. Fruit with excellent flavor and eating quality;
5. Middle season maturity of white flesh fruit;
6. Fruit with an attractive milky white skin; and
7. Vigorous half open growth habit.

2 Drawing Sheets

BACKGROUND OF VARIETY

In the country of origin, Republic of Korea, the tree of this disclosure is believed to have been derived from the Korean commercial variety 'Yumyeong', and within the subspecies *dianthiflora* (Dipp.); and, originated in Seomyun, Yunkikun, Chungnam, Republic of Korea. The appropriate botanical classification for this tree is believed to be *Prunus persica.* This subject tree is believed to be exceptional in a number of characteristics and will offer a further option to commercial growers of stone fruits in terms of fruit having large to very large size, firm flesh, clingstone, sweet, attractively colored fruit which has a comparatively high capacity to withstand handling, shipping and storage. Having the additional desirable fruit characteristics of heavy production of fruit with an attractive ovate shape and pleasant, sweet taste, and which is harvested earlier than normal harvest for fruit of extra large size, this tree promises to be a valuable new variety to industry and commerce which has value as a dessert variety but which may also be used as a canner. This tree further has the advantage of being mid to late-season in blooming so that it is less susceptible to late frosts than other locally adapted tree varieties. I am not aware of varieties which offer a similar or comparable combination of characteristics.

ORIGIN OF THE VARIETY

The new tree was selected from among several thousand seedlings from the 'Yumyeong' variety, which had been planted on my farm in Seomyun, Yunkikun, Chungnam, Korea. The seedling was discovered near a specimen of the noted apparent seed parent, which is a late season variety and which normally ripens between August 20 and September 10. My attention was drawn to this tree when I noticed that it was unusually precocious; producing two to three times more flowers than the parent 'Yumyeong' variety on blooming wood, and by having flowers of a much brighter color than the parent variety. With the recognition of these different characteristics, I allowed the tree to remain for further observation. Upon development and ripening of the fruit, it became clear to me that this tree showed promise due to its production of very high quality fruit of large to extra large size and unusual attractiveness. Based on these observations, I selected the variety for asexual reproduction and commercialization.

ASEXUAL REPRODUCTION OF THE VARIETY

Asexual reproduction of the new and distinct variety was performed by budding in my orchard located in Seomyun Yunkikun, Chungnam, Korea and shows that all characteristics run true to the original tree and are established and transmitted through succeeding propagations.

SUMMARY OF THE VARIETY

The present new and distinct variety of peach tree has been denominated 'Baekyakdo', and the height of the fully grown tree is about 3 meters, which is about 50 cm smaller than that of the tree, Yumyeong, and the diameter of the tree is about 6 to 7 meters. The instant cultivar exhibits vigorous half open growth and is a regular and productive bearer of extra large, white skin, white flesh, clingstone fruit with a mild, sweet, subacidic flavor with excellent eating and stock quality. The fruit is further characterized by having very firm flesh, the ability to hang on the tree 10 to 17 days after maturity (shipping ripe), having good handling and shipping quality, a white skin ground color and ripening in the middle maturity season, approximately 10 days after '*Changbang joseng',* 20 days before Yumyeong, which are established commercial varieties in Korea.

DESCRIPTION OF THE PHOTOGRAPHS

Figure 1:
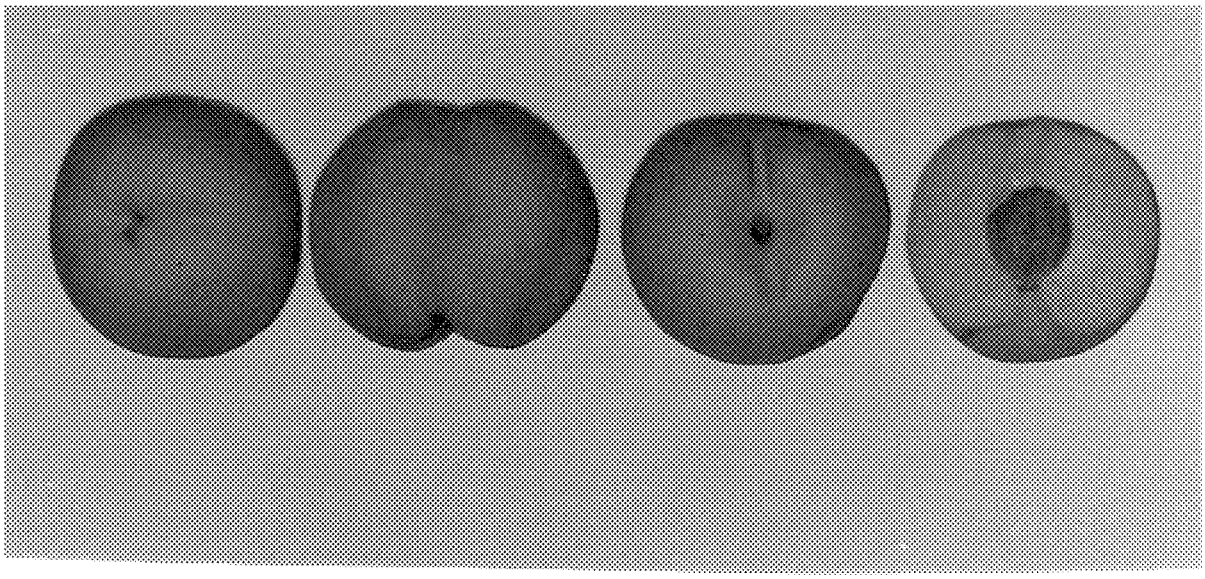
FIG. 1 shows typical specimens of the fruit of the new and distinct peach variety shortly after being picked (firm ripe); illustrating the exterior of the fruit, a fruit divided in its suture plane to reveal flesh coloration, pit cavity, and a stone remaining in place.
Figure 2:
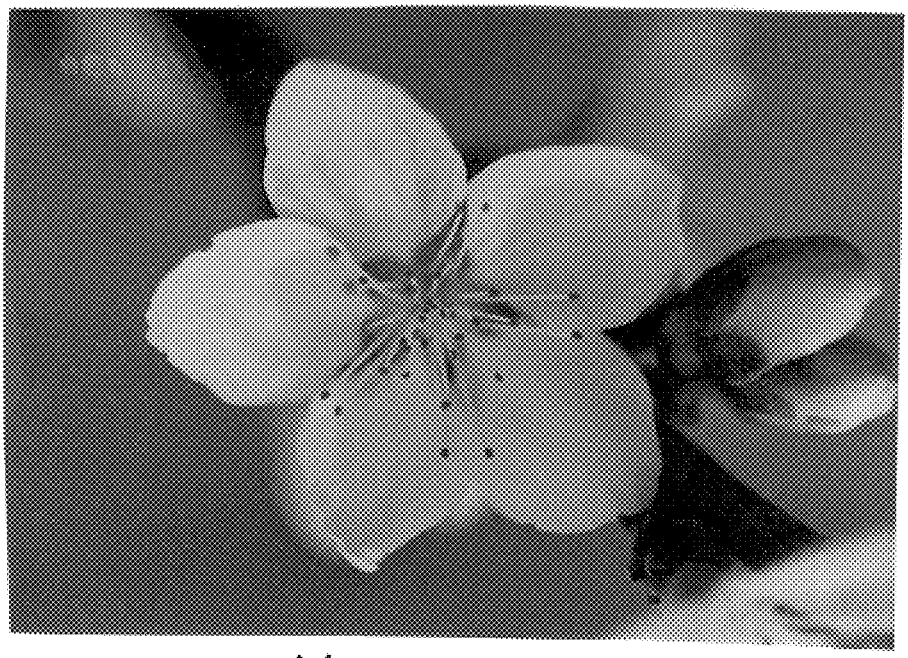
FIG. 2 depicts a flower of the peach tree 'Baekyakdo'.
Figure 3:
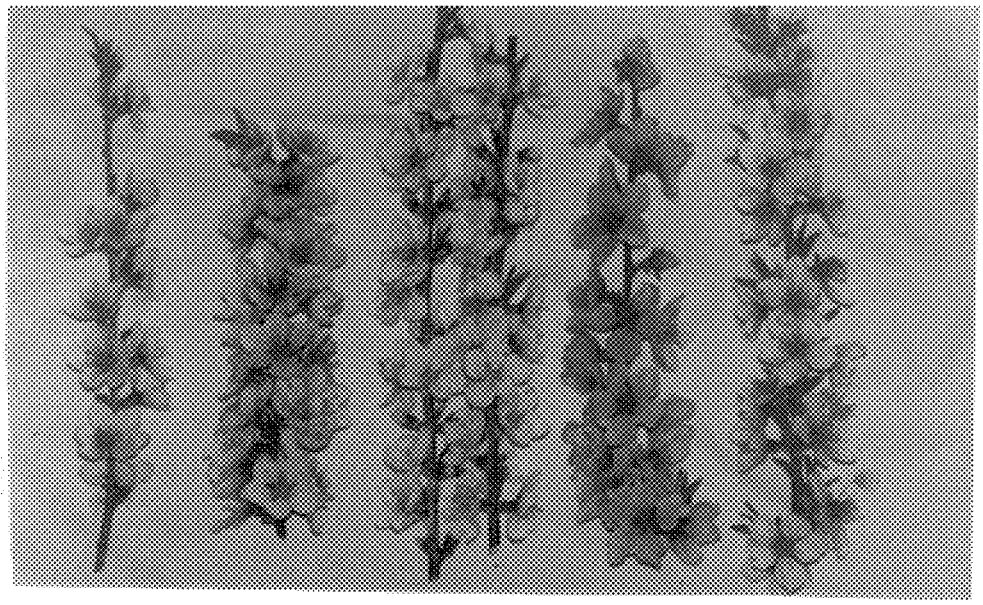

FIG. 3 depicts the blossoms of 'Yumyeong' (unpatented), 'Woulme' (unpatented), 'Baekyakdo', '*Changbang joseng*' (unpatented), and 'Wangdo' (the subject of copending U.S. Plant Patent application Ser. No. 08/862,644), from left to right.

Figure 4:
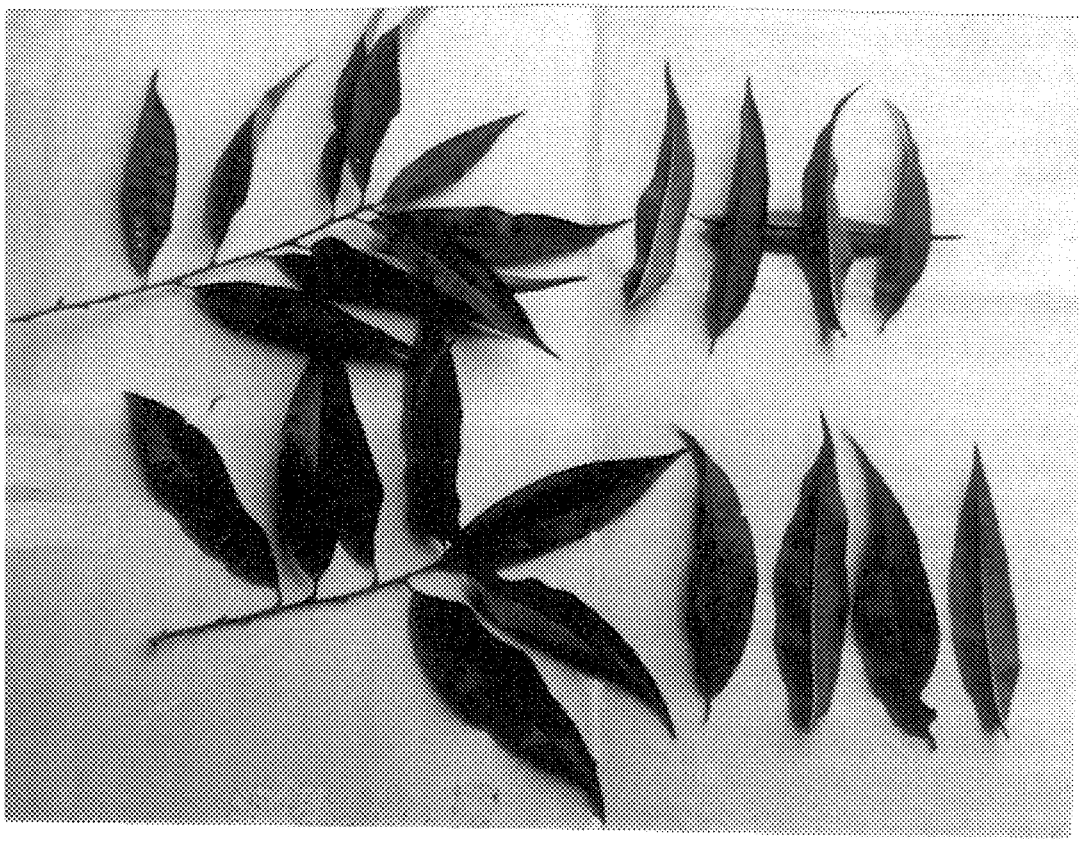

FIG. 4. depicts typical leaves from 'Wangdo' (above) and 'Woulme' (below). The leaf shape of 'Baekyakdo' is the same as that of 'Woulme'.

The colors depicted are as true as is reasonably possible to attain in color reproductions of this type.

DESCRIPTION OF THE VARIETY

The following is a detailed botanical description of the new and distinct variety of peach tree, its flowers, fruit and foliage as based on observations of the specimen grown in my orchard located Seomyun Yunkikun Chungnam, Korea, with color terminology (except those in common terms) in accordance with Pantone® Professional Color System Selector (Pantone, Inc., 1984, 1990).

Tree:
- *Size.*—Large.
- *Vigor.*—Vigorous. Having terminal growth of 1.5 to 2 meters per year, with the growth of the trunk terminating at the height of 3 to 3.5 meters in 3 or 4 years, in Chungnam, Korea.
- *Form.*—Usually pruned to half open shape. The new peach tree grows 1.5 to 2 meters every year from the first to the third year, with the trunk terminating at about 3 meters height and then the trunk thickening every year, and the branches extending upwardly at an angle of 40 to 60 degrees, growing 1.5 meters to 2 meters a year to a maximum extent of 6 to 7 meters. Less branching compared to 'Yumyeong' variety or other peach trees. To obtain large fruit, about 50% pruning is necessary.
- *Production.*—Productive.
- *Bearing.*—Regular.
- *Density.*—Medium dense.

Trunk:
- *Size.*—Medium to stocky.
- *Texture.*—Smooth.
- *Color.*—Brown (18-1124) to (18-1222).

Branches:
- *Size.*—Medium.
- *Texture.*—Varies from smooth to medium rough with maturity.
- *Lenticels.*—Medium size. Medium number.
- *Color.*—Brown (18-1031) to (18-1130) having small parts with light green (16-6329) to (16-6339).

Leaves:
- *Size.*—Medium to large. The shape and size are almost the same as those of 'Yumyeong' variety, but color of the leaves is much lighter green than that of 'Yumyeong' or other varieties.
- *Average.*—14 to 16cm
- *Average width.*—2.5 to 2.8 cm.
- *Form.*—Lanceolate-pointed.
- *Texture.*—Smooth.
- *Thickness.*—Medium.
- *Margin.*—Crenate.
- *Petiole.*—Medium length. Medium thickness.
- *Glands.*—Reniform. Number varies from 0 to 5. Average number 2. Located on base of leaf blade and upper portion of petiole.
- *Color.*—Upper surface green to dark green (18-01117) to (18-0322). Lower surface dull green to grayish green (17-6319) to (17-0119).

Flower buds:
- *Size.*—Medium.
- *Form.*—Plump.
- *Length.*—Medium.
- *Pubescene.*—Pubescent.

Flowers:
- *Size.*—Medium. — non-showy.
- *Blooming period.*—Apr. 17, 1995 to Apr. 27, 1995. Varies slightly due to climatic conditions. This variety is about 3 or 4 days later in flowering than Yumyeong peach trees. The tree is not self-fertile.
- *Color.*—Pinkish in bud and early bloom stage, becoming milky white.
- *Pollen.*—Very little.

Fruit:
- *Maturity when described.*—Firm ripe.
- *Date of first picking.*—Aug. 1, 1995.
- *Date of last picking.*—Aug. 10, 1995.
- *Size.*—Extra Large. Average diameter axially 9.5 to 13 cm. Average transversely in suture plane 8.5 to 12 cm.
- *Form.*—Globose — slightly tip at apex and slightly flattended on stem end. The fruit is exceptionally symmetrical.
- *Suture.*—Shallow but pronounced, extends from base to apex.
- *Ventral surface.*—Nearly rounded, very slightly lipped.
- *Apex.*—Varies from rounded to slight pistil point.
- *Base.*—Retuse.
- *Cavity.*—Rounded to slightly elongated in suture plane. Average depth — 1.5 cm. Average breadth 2.0 cm.

Skin:
- *Thickness.*—Medium.
- *Texture.*—Tenacious to flesh.
- *Tendency to crack.*—None.
- *Down.*—Moderate amount, short to very short in length.
- *Color.*—White (11-0304) to (11-0616).

Flesh:
- *Texture.*—Very frim.
- *Ripens.*—Evenly.
- *Fibers.*—Small, tender.
- *Juice.*—Moderate.
- *Flavor.*—Excellent, mild, very sweet.
- *Aroma.*—Moderate.
- *Eating quality.*—Excellent.
- *Amygdalin.*—Undetected.
- *Color.*—White to milky white (no Pantone number) to (11-0507).

Stone:
- *Type.*—Clingstone.
- *Size.*—Large. Average length 2.7 cm. Average width 2.6 cm. Average thickness 1. 7cm.
- *Form.*—Ovoid.
- *Base.*—Mostly straight — some rounded.
- *Apex.*—Acuminate.
- *Sides.*—Equal.
- *Surface.*—Irregularly furrowed toward apex, ridges usually rounded, pitted toward base.
- *Tendency to spit.*—*None.*
- *Color.*—Brown to reddish brown (18-1540) to (19-1540).

Use: The fruit of the present new variety is well suited for novelty, processing and canning, as well as for use as a dessert peach.

*Market.*—Local and long distance.

Keeping quality: Very good.

Shipping quality: Very good.

The new and distinct variety of peach tree, its flowers, foliage and fruit described above may vary in slightdetail due to variations in climate, soil conditions and cultural practices under which the variety may be grown. The botanical description above is that of the variety grown under the ecological conditions prevailing near Seomyun Yunkikun Chungnam, Korea.

I claim:

1. A new and distinct variety of peach tree, substantially as illustrated and described, characterized by its large size, vigorous, half open growth and being a regular and productive bearer of large, middle season maturing, white flesh, clingstone fruit with excellent flavor and eating quality; the fruit is further characterized by having very firm flesh, good handling and shipping quality and having white skin.

* * * * *